United States Patent
Pilz et al.

(10) Patent No.: US 9,555,117 B2
(45) Date of Patent: Jan. 31, 2017

(54) USE OF ISOSORBIDE MONOESTERS AS THICKENERS

(75) Inventors: Maurice Frederic Pilz, Frankfurt am Main (DE); Peter Klug, Grobostheim (DE); Franz-Xaver Scherl, Burgkirchen (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days.

(21) Appl. No.: 14/237,042

(22) PCT Filed: Jul. 31, 2012

(86) PCT No.: PCT/EP2012/003244
§ 371 (c)(1),
(2), (4) Date: Sep. 16, 2014

(87) PCT Pub. No.: WO2013/017255
PCT Pub. Date: Feb. 7, 2013

(65) Prior Publication Data
US 2015/0030553 A1  Jan. 29, 2015

(30) Foreign Application Priority Data

Aug. 4, 2011 (DE) .................. 10 2011 109 437

(51) Int. Cl.
| | | |
|---|---|---|
| A61K 31/34 | (2006.01) | |
| A61K 47/22 | (2006.01) | |
| C09D 7/00 | (2006.01) | |
| C11D 3/22 | (2006.01) | |
| C11D 17/00 | (2006.01) | |
| A01N 43/90 | (2006.01) | |
| A01N 25/00 | (2006.01) | |
| A61K 8/49 | (2006.01) | |
| A61Q 5/02 | (2006.01) | |
| A61Q 19/10 | (2006.01) | |
| C09D 7/12 | (2006.01) | |
| C11D 3/20 | (2006.01) | |
| A61K 8/04 | (2006.01) | |

(52) U.S. Cl.
CPC .............. *A61K 47/22* (2013.01); *A01N 25/00* (2013.01); *A01N 43/90* (2013.01); *A61K 8/042* (2013.01); *A61K 8/4973* (2013.01); *A61Q 5/02* (2013.01); *A61Q 19/10* (2013.01); *C09D 7/002* (2013.01); *C09D 7/1233* (2013.01); *C11D 3/2096* (2013.01); *C11D 3/221* (2013.01); *C11D 17/003* (2013.01); *A61K 2800/10* (2013.01); *A61K 2800/48* (2013.01)

(58) Field of Classification Search
CPC ..... C11D 3/2096; C11D 3/221; C11D 17/003; C11D 1/667; C11D 3/485; C11D 3/2044; C11D 3/2068; C11D 3/2093; C09D 7/1233; C09D 7/1216; C09D 131/04; C09D 133/02; C09D 133/08; A01N 43/90; A01N 2300/00; A01N 37/10

See application file for complete search history.

(56) References Cited

U.S. PATENT DOCUMENTS

| | | | |
|---|---|---|---|
| 3,331,742 A | | 7/1967 | Babayan |
| 4,637,930 A | | 1/1987 | Konno et al. |
| 4,711,775 A | | 12/1987 | Dittmar et al. |
| 4,847,088 A | | 7/1989 | Blank |
| 5,447,648 A | * | 9/1995 | Steindorf ...................... 510/514 |
| 6,413,529 B1 | | 7/2002 | Beerse et al. |
| 8,642,525 B2 | | 2/2014 | Herrwerth et al. |
| 2005/0222276 A1 | | 10/2005 | Schmaus et al. |
| 2007/0178144 A1 | | 8/2007 | Hameyer et al. |
| 2008/0142023 A1 | | 6/2008 | Schmid |
| 2008/0312195 A1 | | 12/2008 | Simsch et al. |
| 2010/0113664 A1 | | 5/2010 | Bradshaw et al. |

(Continued)

FOREIGN PATENT DOCUMENTS

| | | |
|---|---|---|
| CA | 1231046 | 1/1988 |
| DE | 3328372 | 3/1984 |

(Continued)

OTHER PUBLICATIONS

English-translation of International Preliminary Report on Patentability for PCT/EP2012/003244 dated Feb. 4, 2014.
International Search Report for PCT/EP2012/003244 dated Oct. 18, 2012.
English translation of WO 2010108738.
English translation of WO 2010136121.
International Preliminary Report on Patentability for PCT/EP2010/002918, Dec. 2, 2011.
International Preliminary Report on Patentability for PCT/EP2010/002919, dated Feb. 28, 2012.
International Search Report for PCT/EP2010/002918 mail date Jun. 30, 2011.

(Continued)

Primary Examiner — Nannette Holloman
(74) Attorney, Agent, or Firm — Tod A. Waldrop

(57) ABSTRACT

The use of one or more compounds of the formula (I)

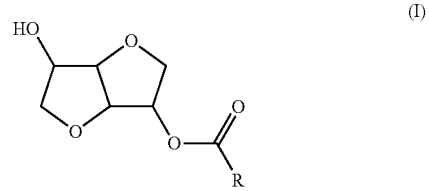

(I)

in which
R is a straight-chain or branched saturated alkyl group having 5 to 11 carbon atoms or a straight-chain or branched mono- or polyunsaturated alkenyl group having 5 to 11 carbon atoms
as thickeners is described.
The use is preferably in cosmetic, dermatological or pharmaceutical compositions, in crop protection formulations, in washing or cleaning compositions or in paints or coatings.

9 Claims, No Drawings

(56) References Cited

U.S. PATENT DOCUMENTS

| | | | |
|---|---|---|---|
| 2011/0104085 A1 | 5/2011 | Klug et al. | |
| 2011/0117036 A1* | 5/2011 | Chaudhuri | 424/60 |
| 2012/0100085 A1 | 4/2012 | Klug et al. | |
| 2012/0101135 A1 | 4/2012 | Klug et al. | |
| 2012/0116101 A1 | 5/2012 | Fuertes et al. | |
| 2014/0308224 A1 | 10/2014 | Pilz et al. | |
| 2014/0315996 A1 | 10/2014 | Pilz et al. | |
| 2014/0322151 A1 | 10/2014 | Fricke et al. | |
| 2014/0323564 A1 | 10/2014 | Pilz et al. | |
| 2014/0323592 A1 | 10/2014 | Pilz et al. | |
| 2014/0329870 A1 | 11/2014 | Pilz et al. | |
| 2014/0343171 A1 | 11/2014 | Pilz et al. | |
| 2014/0348763 A1 | 11/2014 | Pilz et al. | |
| 2014/0369943 A1 | 12/2014 | Pilz et al. | |

FOREIGN PATENT DOCUMENTS

| | | | | |
|---|---|---|---|---|
| DE | 2234009 | | 12/1987 | |
| EP | 1813251 | | 8/2007 | |
| EP | 1972330 | | 9/2008 | |
| EP | 2239315 | A1 * | 10/2010 | C11D 1/66 |
| JP | 59-175408 | | 10/1984 | |
| JP | H01313408 | | 12/1989 | |
| JP | H03168075 | | 7/1991 | |
| JP | 8173787 | | 7/1996 | |
| JP | 8187070 | | 7/1996 | |
| JP | H09291016 | | 11/1997 | |
| JP | 2002541181 | | 12/2002 | |
| JP | 2003238396 | | 8/2003 | |
| JP | 2007203288 | | 8/2007 | |
| WO | WO 2006103338 | | 10/2006 | |
| WO | WO 2008155159 | | 12/2008 | |
| WO | 2010108738 | A2 | 9/2010 | |
| WO | 2010136121 | A2 | 12/2010 | |

OTHER PUBLICATIONS

Bach M. et al. Konservierungsmittel Und Ihre Praktische Anwendung in Kosmetischen Produkten, Sofw-Journal Seifen, Oele, Fette, Wachse, Verlag Fur Chemische Industrie, Angsburg, DE, vol. 116, No. 9, Jun. 13, 1990. pp. 942-7694, XP000134744.
Christian W. Klampfl et al., "Quantitative determination of UV filters in sunscreen lotions using microemulsion electrokinetic chromatography," J. Sep. Sci. Sep. 26, 2003, 1259-1262.
Database CA (Online) Chemical Abstracts Service, Feb. 24, 1985, "Cosmetics Containing Isosrbide Fatty Acid Diesters," Database Accession No. 1985:67233. English-language abstract of JP 59-175408.
Database CA (Online), Chemical Abstracts Service, Columbus, Ohio (May 12, 1984), Miura Takeshi, Ishida Katsuo; "Rinsing assistants", XP002643079. English abstract of JP 51056809.
Database CA (Online), Chemical Abstracts Service, Columbus, Ohio (May 12, 1984), Miura Takeshi, Ishida Katsuo; "Rinsing assistants", XP002643080. English abstract of JP 51068608.
Database CA (Online), Chemical Abstracts Service, Columbus, Ohio (Sep. 29, 2000), Fukushima Noriko; "Water-soluble rinses for dishwashers", XP002643077.
Database CA (Online), Chemical Abstracts Service, Columbus, Ohio (Sep. 18, 2003), Miura Takeshi, et al.; "Coenzyme Q10-containing emulsions, and manufacture thereof", XP002643081. English abstract of JP 2003238396.
Database CA (Online), Chemical Abstracts Service, Columbus, Ohio (Aug. 14, 2008), Mori Toshiki; "Transparent cleaners comprising nonionic surfactants", XP002643078.
Database GNPD (Online), (Feb. 1999), Mintel; "Verzorgende Shampoo-Lang Harr", XP002662186.
Dubini Francesco et al., "In Vitro Antimycotic Activity and Nail Permeation Models of a Prioctone Olamine (Octopirox) Containing Transungual Water Soluble Technology," Arzneimittel Forschung. Drug Research, ECV Editio Cantor Verlag, vol. 55 No. 8, pp. 478-483, Jan. 1, 2005.
English Abstract for JPH03168075, Jul. 19, 1991.
English Abstract for JPH09291016, Nov. 11, 1997.
Presentation by Fredric Pilz, at HPCI Koferenz—Turkey, Jun. 2, 2011.
English-language Abstract of JP 8173787.
English-language Abstract of JP 8187070.
English-language abstract of WO 2008/155159 A1.
English-translation of International Preliminary Report on Patentability for PCT/EP2012/003245 dated Feb. 21, 2014.
English-translation of International Preliminary Report on Patentability for PCT/EP2012/003246 dated Feb. 4, 2014.
English-Translation of International Preliminary Report on Patentability for PCT/EP2012/003247 dated Mar. 24, 2014.
English-Translation of International Preliminary Report on Patentability for PCT/EP2012/003248 dated Feb. 4, 2014.
English-translation of International Preliminary Report on Patentability for PCT/EP2012/003252 dated Feb. 4, 2014.
English-translation of International Preliminary Report on Patentability for PCT/EP2012/003253 dated Feb. 4, 2014.
F.C. Kull et al., Applied Microbiology 1961, 9, 538.
Frieder W. Lichtenthaler, "Carbohydrates, Chapter 9: Carbohydrates as Organic Raw Materials," Ullmann's Encyclopedia of Industrial Chemistry, vol. 6, pp. 262-273, Jan. 1, 2003.
Giacometti, J. et al., "Process for Preparing Nonionic Surfactant Sorbitan Fatty Acid Esters with and without Previous Sorbitol Cyclization", J. of Agricultural and Food Chemistry, American Chemical Society, vol. 44, Jan. 1, 1996, pp. 3950-3954.
International Search Report for PCT/EP2010/002919 mail date Nov. 15, 2011.
International Search Report for PCT/EP2012/003245 dated Oct. 5, 2012.
International Search Report for PCT/EP2012/003246 dated Oct. 18, 2012.
International Search Report for PCT/EP2012/003247 dated Oct. 18, 2012.
International Search Report for PCT/EP2012/003248 dated Oct. 18, 2012.
International Search Report for PCT/EP2012/003249 dated Oct. 5, 2012.
International Search Report for PCT/EP2012/003250 dated Oct. 5, 2012.
International Search Report for PCT/EP2012/003251 dated Oct. 10, 2012.
International Search Report for PCT/EP2012/003252 dated Oct. 8, 2012.
International Search Report for PCT/EP2012/003253 dated Oct. 8, 2012.
International Search Report for PCT/EP2012/004827 dated Jan. 7, 2014.
Peter Stoss et al., "Regioselektive Acylierung von 1, 4:3, 6-Dianhydro-D-glucit," Synthesis, vol. 1987, No. 02, pp. 174-176, Jan. 1, 1987.
Seal, Kenneth J. et al., "Benzisothiazolinone and Methylisothiazolinone. New Preservative System," Cosmetic Technology, CEC, vol. 5, No. 1, pp. 47-52, Jan. 1, 2002.
Translation of International Preliminary Report on Patentability for PCT/EP2012/003249 dated Feb. 4, 2014.
Translation of International Preliminary Report on Patentability for PCT/EP2012/003250 dated Feb. 4, 2014.
Translation of International Preliminary Report on Patentability for PCT/EP2012/003251 dated Feb. 4, 2014.
USPTO Ex Parte Quayle Action for U.S. Appl. No. 14/237,071, dated Jun. 24, 2015.
USPTO Final Rejection for U.S. Appl. No. 13/321,178, dated Dec. 4, 2013.
USPTO Final Rejection for U.S. Appl. No. 13/321,199, dated Mar. 19, 2015.
USPTO Final Rejection for U.S. Appl. No. 13/321,199, dated Dec. 24, 2013.
USPTO Final Rejection for U.S. Appl. No. 14/237,053, dated Sep. 8, 2015.
USPTO Non-Final Rejection for U.S. Appl. No. 13/321,178, dated Apr. 30, 2013.

(56) References Cited

OTHER PUBLICATIONS

USPTO Non-Final Rejection for U.S. Appl. No. 13/321,178, dated May 6, 2014.
USPTO Non-Final Rejection for U.S. Appl. No. 13/321,199, dated Apr. 22, 2013.
USPTO Non-Final Rejection for U.S. Appl. No. 13/321,199, dated Aug. 18, 2015.
USPTO Non-Final Rejection for U.S. Appl. No. 13/321,199, dated Sep. 5, 2014.
USPTO Non-Final Rejection for U.S. Appl. No. 14/237,024, dated Mar. 4, 2015.
USPTO Non-Final Rejection for U.S. Appl. No. 14/237,039, dated Aug. 14, 2015.
USPTO Non-Final Rejection for U.S. Appl. No. 14/237,053, dated May 7, 2015.
USPTO Non-Final Rejection for U.S. Appl. No. 14/237,076, dated Sep. 9, 2015.
USPTO Requirement for Restriction/Election for U.S. Appl. No. 13/321,178, dated Jan. 10, 2013.
USPTO Requirement for Restriction/Election for U.S. Appl. No. 13/321,199, dated Nov. 7, 2012.
USPTO Requirement for Restriction/Election for U.S. Appl. No. 14/237,027, dated Jan. 28, 2015.
USPTO Requirement for Restriction/Election for U.S. Appl. No. 14/237,039, dated Aug. 14, 2015.
USPTO Requirement for Restriction/Election for U.S. Appl. No. 14/237,071, dated Jan. 28, 2015.
Sorbitan Caprylate—the Preservative Boosting, Multifunctional Ingredient, Frederic Pilz, Cosmetic Science Technology, 2011, pp. 131-134.
A welcome side effect: How Velsan® SC (Sorbitan Caprylate) helps to reduce the concentration of classical preservatives, Fredric Pilz, et al., Household and Personal Care Today, Mar. 2010, pp. 22-24.
Velsan SC: Caprilato de sorbitan—Ingrediente multifuncional, conservante, hidnitropo y agente co-emulsionante, Fredric Pilz, et al., NCP 322, Nov.-Dec. 2011, pp. 15-19.
A preservative-free solution, Fredric Pilz, SPC, Oct. 2011.
Presentation by Fredric Pilz, at In-Cosmetics 2010 Paris, Apr. 5, 2010.
Presentation by Fredric Pilz, at SCS Formulate, Nov. 10, 2010.
Presentation by Fredric Pilz, at HPCI Koferenz—Asien, Dec. 17, 2010.
Presentation by Fredric Pilz, at In-Cosmetics 2011 Milano, Mar. 31, 2011.
U.S. Appl. No. 14/237,032, filed Feb. 4, 2014.

\* cited by examiner

USE OF ISOSORBIDE MONOESTERS AS THICKENERS

The present invention relates to the use of isosorbide monoesters as thickeners.

In industry, thickeners are used to adjust the viscosity of products such as, for example, cosmetic, dermatological or pharmaceutical compositions, crop protection formulations, washing or cleaning compositions or paints or coatings in a targeted manner. Numerous thickeners which can be used for this purpose are known. These thickeners may have been produced synthetically, or they may be based on natural raw materials.

However, a disadvantage of the use of many synthetically produced thickeners, for example synthetic polymers, is that, frequently, their preparation is expensive and based on synthetic raw materials. In contrast, a disadvantage of the use of many thickeners based on natural raw materials is that the appearance of many products comprising such thickeners is in need of improvement.

Accordingly, it was an object of the invention to provide thickeners which do not have the disadvantages mentioned above or which improve these at least in part and which additionally have an advantageous thickener performance.

Surprisingly, it has now been found that this object is achieved by compounds of the formula (I)

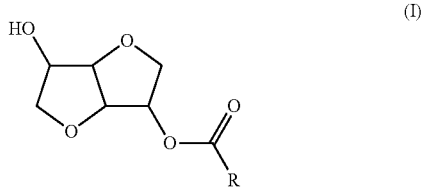

in which
R is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms.

Accordingly, the invention provides the use of one or more compounds of the formula (I)

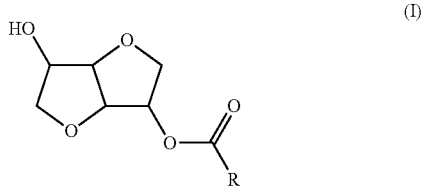

in which
R is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms as thickeners.

The compounds of the formula (I) are based on renewable raw materials such as, for example, on isosorbide, which can be obtained from sugar. They can be prepared in a simple manner by methods familiar to the person skilled in the art, for example by esterification of isosorbide with an acid component such as a carboxylic acid. The appearance of the products comprising the compounds of the formula (I) is not negatively affected by their presence. For example, compared to the use of xanthan gum which, as natural thickener, frequently yields products having a "brittle" or irregular or rough surface, using the compounds of the formula (I) it is possible to prepare thickened products having a smooth surface.

Compositions which are based at least in part on renewable raw materials and can be used as thickeners are already known.

WO 2010/108738 A2 (Evonik) describes formulations which are used to clean and care for human or animal body parts and comprise sorbitancarboxylic esters, where the carboxylic acid portion of the sorbitancarboxylic ester is derived from a carboxylic acid containing 6 to 10 carbon atoms and the sorbitancarboxylic esters have a hydroxyl value of more than 350, and the use of the sorbitancarboxylic esters mentioned as viscosity regulators, care active ingredient, foam booster or solubilizer in cleaning or care formulations.

Compounds of the formula (I) can be prepared, for example, by methods familiar to the person skilled in the art. For example, the compounds of the formula (I) can be prepared by esterification of isosorbide by customary methods known to the person skilled in the art, with both isosorbide for its part and also the acid components used for esterification once more being commercially available.

Preferably, the radical R in the one or more compounds of the formula (I) is a straight-chain saturated alkyl radical having 7 to 9 carbon atoms.

Particularly preferably, the radical R in the one or more compounds of the formula (I) is a straight-chain saturated alkyl radical having 7 carbon atoms.

According to the invention, the one or more compounds of the formula (I) can be used on their own or in compositions comprising one or more other substances as thickeners. Hereinbelow, these compositions are referred to as "compositions A".

In a preferred embodiment of the invention, the compositions A comprise one or more compounds of the formula (I) and additionally one or more other substances selected from the group consisting of sorbitol, sorbitol esters (sorbitol esters can be mono-, di-, tri-, tetra-, penta- and/or hexaesters), sorbitan, sorbitan esters (sorbitan esters can be mono-, di-, tri- and/or tetraesters), isosorbide, isosorbide diesters and carboxylic acids. "Sorbitan" can be, for example, 1,4- or 1,5-sorbitan. Both the carboxylic acids themselves and the carboxylic acids on which the acid components of the esters mentioned are based correspond to the formula RCOOH in which R has the meaning given for formula (I) and is preferably a straight-chain saturated alkyl radical having 7 carbon atoms, i.e. the carboxylic acid RCOOH is preferably caprylic acid.

In a particularly preferred embodiment of the invention, the compositions A comprise one or more compounds of the formula (I) and additionally I) isosorbide and
II) one or more isosorbide diesters of the formula (II)

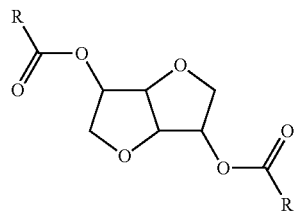

where R has the meaning given above for formula (I) and where the isosorbide diester is preferably isosorbide dicaprylate.

From among these compositions, the compositions A just mentioned preferably comprise one or more compounds of the formula (I) and additionally I) from 0.05 to 0.7, preferably from 0.1 to 0.7 and particularly preferably from 0.2 to 0.5 part by weight of isosorbide and II) from 0.1 to 1.0, preferably from 0.2 to 1.0 and particularly preferably from 0.4 to 0.8 part by weight of the one or more isosorbide diesters of the formula (II), where the isosorbide diester is preferably isosorbide dicaprylate, in each case based on 1.0 part by weight of the one or more compounds of the formula (I) and preferably based on 1.0 part by weight of isosorbide monocaprylate.

In a preferred embodiment of this embodiment of the invention, the compositions A just mentioned comprise either no carboxylic acid RCOOH or up to 0.1, preferably 0.001 to 0.05 and particularly preferably 0.002 to 0.01 part by weight of carboxylic acid RCOOH, where R has the meaning given for formula (I) and where the carboxylic acid is preferably caprylic acid, based on 1.0 part by weight of the one or more compounds of the formula (I) and preferably based on 1.0 part by weight of isosorbide monocaprylate.

In a further particularly preferred embodiment of the invention, the compositions A comprise one or more compounds of the formula (I) and one or more sorbitan esters of sorbitan and carboxylic acids $R^a$COOH, preferably selected from sorbitan esters of 1,4- and/or 1,5-sorbitan and carboxylic acids $R^a$COOH, where $R^a$ is a straight-chain or branched saturated alkyl group having 5 to 11, preferably 7 to 9 and particularly preferably 7 carbon atoms or a straight-chain or branched mono- or polyunsaturated alkenyl group having 5 to 11, preferably 7 to 9 and particularly preferably 7 carbon atoms, and where the weight ratio of the one or more compounds of the formula (I) to the one or more sorbitan esters just mentioned is from 70:30 to 100:0, preferably from 80:20 to 100:0, particularly preferably from 90:10 to 100:0 and especially preferably from 95:5 to 100:0. The stated weight ratio of "100:0" means that in this particularly preferred embodiment of the invention, the compositions A just mentioned do not need to comprise any sorbitan ester.

From among the compositions A just mentioned, preference is given to those in which the one or more sorbitan esters of sorbitan and carboxylic acids $R^a$COOH are selected from sorbitan esters of sorbitan and caprylic acid and are preferably selected from sorbitan esters of 1,4- and/or 1,5-sorbitan and caprylic acid and the sorbitan ester is particularly preferably sorbitan monocaprylate.

In these compositions A, the hydroxyl value of the mixture of the one or more compounds of the formula (I) and the one or more (if present) sorbitan esters of sorbitan and carboxylic acids $R^a$COOH is preferably smaller than or equal to 320, particularly preferably smaller than or equal to 285, especially preferably smaller than or equal to 245 and most preferably smaller than or equal to 225.

In a further particularly preferred embodiment of the invention, the hydroxyl value of the mixture of the one or more compounds of the formula (I) and the one or more compounds selected from the group consisting of sorbitol, sorbitol esters, sorbitan, sorbitan esters, isosorbide, isosorbide diesters and carboxylic acids in the compositions A is smaller than or equal to 320, preferably smaller than or equal to 285, particularly preferably smaller than or equal to 245 and especially preferably smaller than or equal to 225.

In a further particularly preferred embodiment of the invention, the compositions A do not comprise any compounds selected from sorbitol and sorbitol esters.

In a further particularly preferred embodiment of the invention, the compositions A do not comprise any compounds selected from sorbitan and sorbitan esters.

If the compositions A do comprise one or more compounds selected from the group consisting of sorbitol and sorbitol esters (where the carboxylic acid on which the acid component of these esters is based is preferably caprylic acid), these compounds together are preferably present in the compositions A in an amount smaller than or equal to 5.0% by weight, particularly preferably in an amount smaller than or equal to 3.0% by weight, especially preferably in an amount smaller than or equal to 1.0% by weight and most preferably in an amount smaller than or equal to 0.5% by weight, the stated % by weight in each case being based on the total weight of the finished compositions A.

If the compositions A do comprise one or more compounds selected from the group consisting of sorbitan and sorbitan esters (where the carboxylic acid on which the acid component of these esters is based is preferably caprylic acid), these compounds together are preferably present in the compositions A in an amount smaller than or equal to 20.0% by weight, particularly preferably in an amount smaller than or equal to 10.0% by weight, especially preferably in an amount smaller than or equal to 5.0% by weight and most preferably in an amount smaller than or equal to 1.0% by weight, the stated % by weight in each case being based on the total weight of the finished compositions A.

In a further particularly preferred embodiment of the invention, the compositions A comprise the one or more compounds of the formula (I) in amounts of at least 30% by weight, preferably in amounts of at least 50% by weight and particularly preferably in amounts of at least 60% by weight, in each case based on the total weight of the finished compositions A.

The hydroxyl value of a substance is to be understood as meaning that amount of KOH in mg equivalent to the amount of acetic acid bound during the acetylation of 1 g of substance.

Suitable determination methods for determining the hydroxyl value are, for example, DGF C-V 17 a (53), Ph. Eur. 2.5.3 Method A and DIN 53240.

In the context of the present invention, the hydroxyl values are determined analogously to DIN 53240-2. Here, the following procedure is adopted: 1 g, accurate to 0.1 mg, of the homogenized sample to be measured is weighed out. 20.00 ml of acetylation mixture (acetylation mixture: 50 ml of acetic anhydride are stirred into 1 liter of pyridine) are added. The sample is dissolved completely in the acetylation mixture, if required with stirring and heating. 5 ml of catalyst solution (catalyst solution: 2 g of 4-dimethylaminopyridine are dissolved in 100 ml of pyridine) are added. The reaction vessel is closed and placed into the water bath, preheated to 55° C., for 10 minutes, with mixing. 10 ml of fully deionized water are then added to the reaction solution, the reaction vessel is closed again and the mixture is once more allowed to react in the water bath with shaking for 10 minutes. The sample is cooled to room temperature (25° C.). 50 ml of 2-propanol and 2 drops of phenolphthalein are then added. This solution is titrated with aqueous sodium hydroxide solution (aqueous sodium hydroxide solution c=0.5 mol/l) (Va). Under identical conditions, but without any sample added, the efficacy of the acetylation mixture is determined (Vb).

From the aqueous sodium hydroxide solution consumed in the determination of the efficacy and the titration of the sample, the hydroxyl value (OHV) is calculated using the following formula:

$$OHV = \frac{(Vb - Va) \cdot c \cdot t \cdot M}{E}$$

OHV=hydroxyl value in mg KOH/g substance
Va=aqueous sodium hydroxide solution consumed in ml during the titration of the sample
Vb=aqueous sodium hydroxide solution consumed in ml during the titration of the efficacy
c=molar concentration of the aqueous sodium hydroxide solution in mol/l
t=titer of the aqueous sodium hydroxide solution
M=molar mass of KOH=56.11 g/mol
E=sample weighed out in g (Vb−Va) is that amount of aqueous sodium hydroxide solution used in ml, which is equivalent to the amount of acetic acid bound during the above-described acetylation of the sample to be measured.

Hereinbelow, the method just described for determining the hydroxyl value is referred to as "method OHV-A".

Preferably, the use according to the invention is in cosmetic, dermatological or pharmaceutical compositions, in crop protection formulations, in washing or cleaning compositions or in paints or coatings. The crop protection compositions comprise one or more pesticides.

The cosmetic, dermatological or pharmaceutical compositions, the crop protection formulations, the washing or cleaning compositions or the paints or coatings comprise the one or more compounds of the formula (I) preferably in amounts of from 0.01 to 10.0% by weight, particularly preferably in amounts of from 0.1 to 5.0% by weight and especially preferably in amounts of from 0.2 to 3.0% by weight, in each case based on the total weight of the finished cosmetic, dermatological or pharmaceutical compositions, crop protection formulations, washing or cleaning compositions or paints or coatings.

The cosmetic, dermatological or pharmaceutical compositions, the crop protection formulations, the washing or cleaning compositions or the paints or coatings have viscosities preferably in the range from 50 to 200 000 mPa·s, particularly preferably in the range from 500 to 100 000 mPa·s, especially preferably in the range from 2 000 to 50 000 mPa·s and most preferably in the range from 5 000 to 30 000 mPa·s (20° C., Brookfield RVT, RV spindle set; 20 revolutions per minute).

The cosmetic, dermatological or pharmaceutical compositions are preferably present in the form of fluids, gels, foams, sprays, lotions or creams.

The cosmetic, dermatological or pharmaceutical compositions, the crop protection formulations, the washing or cleaning compositions or the paints or coatings are preferably formulated on an aqueous or aqueous-alcoholic basis or are present as emulsions or dispersions. Particularly preferably, they are present as emulsions, and especially preferably they are present as oil-in-water emulsions.

As further auxiliaries and additives, the cosmetic, dermatological or pharmaceutical compositions, the crop protection formulations, the washing or cleaning compositions or the paints or coatings may comprise all substances customarily used for the application in question, for example oils, waxes, emulsifiers, coemulsifiers, dispersants, surfactants, defoamers, solubilizers, electrolytes, hydroxy acids, stabilizers, polymers, film formers, further thickeners (different from the compounds of the formula (I)), gelling agents, superfattening agents, refattening agents, antimicrobially active compounds, biogenic active compounds, astringents, active substances, deodorizing substances, sun protection filters, antioxidants, oxidants, humectants, solvents, colorants, pigments, pearlizing agents, fragrances, opacifiers and/or silicones.

The cosmetic, dermatological or pharmaceutical compositions, the crop protection formulations, the washing or cleaning compositions or the paints or coatings have a pH of preferably from 2 to 11, particularly preferably from 4.5 to 8.5 and especially preferably from 5.5 to 6.5.

The examples and applications which follow are intended to illustrate the invention in more detail, without, however, limiting it. All percentages are % by weight, unless explicitly stated otherwise.

Thickener performance was measured under the following conditions:
Brookfield RVT; 20° C.; RV spindle set; 20 revolutions per minute

EXPERIMENTAL EXAMPLES

A) Preparation of Isosorbide Caprylate

In a stirred apparatus with distillation head, 190.0 g (1.3 mol) of isosorbide ("Sorbon" from Ecogreen Oleochemicals) and 187.5 g (1.3 mol) of octanoic acid (caprylic acid) are initially charged at 80° C. together with 0.38 g of aqueous sodium hydroxide solution (18% by weight strength, aqueous) as catalyst. With stirring and under a flow of nitrogen (10-12 liters per hour), the reaction mixture is initially heated to 180° C., where the water of reaction begins to distill off. The reaction mixture is then heated to 190° C. over a period of 1 hour and to 210° C. over a further 2 hours. After 210° C. is reached, the esterification is continued until an acid value of <1 mg KOH/g is reached. This gives 345.7 g of amber isosorbide caprylate (97% of theory). The pH (5% by weight in ethanol/water 1:1) is 5.9. The pH was measured according to DIN EN 1262.

Further analytical characteristics of the isosorbide caprylate:
Acid value: 0.9 mg KOH/g, measured according to DIN EN ISO 2114
Hydroxyl value: 206 mg KOH/g, measured analogously to DIN 53240-2 according to method OHV-A
Saponification value: 204 mg KOH/g, measured according to DIN EN ISO 3681

The isosorbide caprylate has the following composition:

| Substance | % by weight |
|---|---|
| caprylic acid | 0.4 |
| isosorbide | 18.1 |
| isosorbide monocaprylate | 50.9 |
| isosorbide dicaprylate | 30.6 |

Hereinbelow, this composition is referred to as "isosorbide caprylate 1"

B) Determination of the Thickener Performance of Isosorbide Caprylate 1

Using Genapol® LRO (sodium laureth-2 sulfate, 27% by weight in water) and Genagen® CAB 818 (cocamidopropyl betaine, 30% by weight in water) and additionally water, a 15% by weight mixture in water comprising the two surfactants in a weight ratio of 8:2 (hereinbelow referred to as "mixture 1") is obtained. Various substances were added to this mixture 1, and the viscosity of the resulting compositions was determined. The results are shown in table 1 below.

TABLE 1 measured viscosities

| Added substance; amount [% by weight] | Viscosity [mPa · s] |
|---|---|
| NaCl [0.5% by weight] | 40 |
| NaCl [0.5% by weight] and isosorbide caprylate 1 [1% by weight] | 330 |

Various amounts of isosorbide caprylate 1 were added to mixture 1, and the viscosity of the resulting compositions was determined. The results are shown in table 2 below.

TABLE 2 measured viscosities

| Amount of isosorbide caprylate 1 added [% by weight] | Viscosity [mPa · s] |
|---|---|
| 0 | 5 |
| 0.2 | 6 |
| 0.4 | 10 |
| 0.6 | 12 |
| 0.8 | 21 |
| 1.0 | 12 |
| 1.2 | 37 |
| 1.4 | 34 |
| 1.6 | 45 |
| 1.8 | 55 |
| 2.0 | 72 |

It is evident from the results listed in tables 1 and 2 that isosorbide caprylate 1 has a thickening effect in aqueous surfactant systems.

C) Determination of the Thickener Performance of Isosorbide Caprylate 1

Using Genapol® LRO (sodium laureth-2 sulfate, 27% by weight in water) and Genagen® KB (cocobetain, 30% by weight in water) and additionally water, a 15% by weight mixture in water comprising the two surfactants in a weight ratio of 8:2 (hereinbelow referred to as "mixture 2") is obtained. Various substances were added to this mixture 2, and the viscosity of the resulting compositions was determined. The results are shown in table 3 below.

TABLE 3 measured viscosities

| Added substance; amount [% by weight] | Viscosity [mPa · s] |
|---|---|
| NaCl [0.5% by weight] | 3830 |
| NaCl [0.5% by weight] and isosorbide caprylate 1 [1% by weight] | 14200 |

Various amounts of isosorbide caprylate 1 were added to mixture 2, and the viscosity of the resulting compositions was determined. The results are shown in table 4 below.

TABLE 4 measured viscosities

| Amount of isosorbide caprylate 1 added [% by weight] | Viscosity [mPa · s] |
|---|---|
| 0 | 135 |
| 0.2 | 310 |
| 0.4 | 460 |
| 0.6 | 875 |
| 0.8 | 1550 |
| 1.0 | 2510 |
| 1.2 | 4190 |
| 1.4 | 5650 |
| 1.6 | 6600 |
| 1.8 | 7400 |
| 2.0 | 7050 |

It is evident from the results listed in tables 3 and 4 that isosorbide caprylate 1 has a thickening effect in aqueous surfactant systems.

D) Determination of the Thickener Performance of Isosorbide Caprylate 1

An emulsion as indicated in table 5 below was prepared, and various concentrations of isosorbide caprylate 1 were added. The viscosities of the resulting emulsions were determined. The results are shown in table 5 below.

TABLE 5 measured viscosities

| Composition | 1 | 2 | 3 | 4 |
|---|---|---|---|---|
| Hostaphat® KL 340 D (A) trilaureth-4 phosphate | 1 | 1 | 1 | 1 |
| mineral oil n.v. (A) | 8 | 8 | 8 | 8 |
| isopropyl palmitate (A) | 3 | 3 | 3 | 3 |
| Lanette® O (A) cetearyl alcohol | 0.5 | 0.5 | 0.5 | 0.5 |
| Myritol® 318 (A) caprylic/capric triglyceride | 2 | 2 | 2 | 2 |
| Tegin® M (A) glyceryl stearate | 0.5 | 0.5 | 0.5 | 0.5 |
| isosorbide caprylate 1 (A) | — | 0.5 | 1.0 | 1.5 |
| Aristoflex® AVC (B) ammonium acryloyldimethyltaurate/VP copolymer | 0.4 | 0.4 | 0.4 | 0.4 |
| water (C) | 71.6 | 72.1 | 71.6 | 71.1 |
| glycerol (C) | 5 | 5 | 5 | 5 |
| alcohol (D) | 5 | 5 | 5 | 5 |
| tocopheryl acetate (D) | 1 | 1 | 1 | 1 |

TABLE 5-continued measured viscosities

| Composition | 1 | 2 | 3 | 4 |
|---|---|---|---|---|
| SilCare ® Silicone 41M15 (D) caprylyl methicone | 1 | 1 | 1 | 1 |
| Nipaguard ® PDU (E) diazolidinylurea, methylparaben, propylparaben, propylene glycol | 1 | 1 | 1 | 1 |
| pH measured | 6.34 | 6.21 | 6.12 | 6.20 |
| viscosity [mPa · s] | 1860 | 2260 | 3130 | 3200 |

Preparation:

I The components of A are mixed and the mixture is heated to 60° C.
II The components of C are mixed and the mixture is heated to 60° C.
III B is added to I
IV II is added to III and the mixture is stirred until it has cooled to room temperature
V The components D are gradually added to IV
VI E is added to V, and the emulsion is homogenized It is evident from the results listed in table 5 that isosorbide caprylate 1 has a thickening effect in emulsions.

E) Comparative Experiment

The thickener performance of isosorbide caprylate 1 in mixture 2 was compared, firstly, to a composition comprising 89.6% by weight of isosorbide dicaprylate and 9.4% by weight of isosorbide monocaprylate (remainder: 1% by weight) (hereinbelow referred to as "isosorbide dicaprylate") and, secondly, to pure isosorbide. The results are shown in table 6.

TABLE 6 measured viscosities

| Substance added to mixture 2; amount [% by weight] | Viscosity [mPa · s] |
|---|---|
| none | 135 |
| isosorbide caprylate 1 [1% by weight] | 2510 |
| isosorbide dicaprylate [1% by weight] | 2390 |
| isosorbide [1% by weight] | 160 |

As is evident from the results of table 6, the thickener performance of isosorbide is not worth mentioning, whereas isosorbide dicaprylate causes significant thickening.

However, as is also evident from the results of table 6, isosorbide caprylate 1 causes thickening comparable to that of isosorbide dicaprylate. If the thickener performance of isosorbide caprylate 1 were due only to the isosorbide dicaprylate comprised therein, the viscosity when using isosorbide caprylate 1 would have to be markedly lower that when isosorbide dicaprylate is used, since isosorbide caprylate 1 comprises only 30.6% by weight of isosorbide dicaprylate. Since the thickener performance of the isosorbide present in isosorbide caprylate 1 (as already mentioned above) is not worth mentioning and the possible thickening by the caprylic acid present in isosorbide caprylate 1 is negligible because of its small amount, but the thickener performance of isosorbide caprylate 1 is nevertheless comparable to the thickener performance of isosorbide dicaprylate, the compound isosorbide monocaprylate present in isosorbide caprylate 1 must have a significant thickener performance.

F) Use Examples

The use according to the invention can take place, for example, in the following formulations.

Formulation Example 1

Very Gentle EO- and Sulfate-Free Shampoo

| Phase | Ingredient | % by weight |
|---|---|---|
| A | water | ad 100 |
| B | sorbitol | 1.0 |
| C | Hostapon ® SG sodium cocoyl glycinate | 30.0 |
|   | Genagen ® KB coco-betaine | 15.0 |
|   | Plantacare ® 818 UP coco glucoside | 9.23 |
|   | isosorbide caprylate 1 | 1.0 |
| D | lactic acid 25% by weight strength in water | 3.25 |
| E | preservative | q.s. |

Preparation:

I B is added to A and the mixture is stirred until a clear solution is obtained
II C is added to I and the mixture is stirred until the solution is homogeneous
III The pH is adjusted to 7.0-7.2 using D
IV E is added to III Formulation Example 2

Gentle Facial Cleanser

| Phase | Ingredient | % by weight |
|---|---|---|
| A | water | ad 100 |
|   | glycerol | 20.0 |
| B | Hostapon ® SG sodium cocoyl glycinate | 34.0 |
|   | lauric acid | 1.0 |
|   | myristic acid | 0.25 |
|   | stearic acid | 0.25 |
|   | isosorbide caprylate 1 | 1.0 |
| C | lactic acid | 0.90 |
|   | water | 6.80 |
| D | Genagen ® CAB cocamidopropyl betaine | 10.0 |
| E | preservative | q.s. |
|   | fragrance | q.s. |

Preparation:

I Phase A is mixed and heated to 80° C.
II The components of B are added gradually to I and stirring is continued at 80° C.
III Phase C is mixed and added to II
IV The mixture is allowed to cool to 60° C., and D is added to III
V At 40° C., E is added to IV

Formulation Example 3

Dishwashing Liquids

| Ingredient | % by weight |
|---|---|
| Hostapur ® SAS 60 (alkanesulfonate, 60% by weight in water) | 40.0 |
| Hostapur ® OS liquid (sodium C14-16 alkyl sulfonate, 40% by weight in water) | 11.0 |
| isosorbide caprylate 1 | 1.0 |
| Genagen ® CAB (cocoamidopropyl betaine, 30% by weight in water) | 3.0 |
| preservative | q.s. |
| water | ad 100 |

Formulation Example 4

Surface Cleaners (all-Purpose Cleaners)

| Ingredient | % by weight |
|---|---|
| Hostapur ® SAS 60 (alkanesulfonate, 60% by weight in water) | 5.0 |
| Genapol ® UD 080 (undecanol + 8 EO) | 2.0 |
| isosorbide caprylate 1 | 1.0 |
| preservative | q.s. |
| water | ad 100 |

Preparation of formulation examples 3 and 4:

Half of the amount of water is initially charged and the components are stirred in in the same order as listed in the tables. The remaining amount of water is then added. This gives clear aqueous compositions.

The invention claimed is:

1. A method of thickening a cosmetic, dermatological or pharmaceutical composition, crop protection formulation, washing or cleaning composition or paint or coating, comprising the step of adding a thickening composition comprising at least one compound of the formula (I)

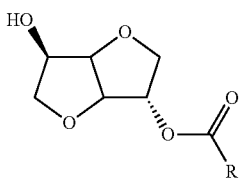

(I)

in which
R is a straight-chain or branched saturated alkyl group having 5 to 11 carbon atoms or a straight-chain or branched mono- or polyunsaturated alkenyl group having 5 to 11 carbon atoms,
wherein the thickening composition further comprises at least one other substance selected from the group consisting of sorbitol, sorbitol esters, isosorbide, isosorbide diesters and carboxylic acids and wherein the hydroxyl value of the mixture of the at least one compound of the formula (I) and the at least one other substance selected from the group consisting of sorbitol, sorbitol esters, isosorbide, isosorbide diesters and carboxylic acids is less than or equal to 320, to the cosmetic, dermatological or pharmaceutical composition, crop protection formulation, washing or cleaning composition or paint or coating.

2. The method of claim 1, wherein the radical R in formula (I) is a straight-chain saturated alkyl radical having 7 to 9 carbon atoms.

3. The method of claim 2, wherein the radical R in formula (I) is a straight-chain saturated alkyl radical having 7 carbon atoms.

4. The method of claim 1, wherein the thickening composition comprises at least one compound of the formula (I),
I) isosorbide and
II) at least one isosorbide diester of the formula (II)

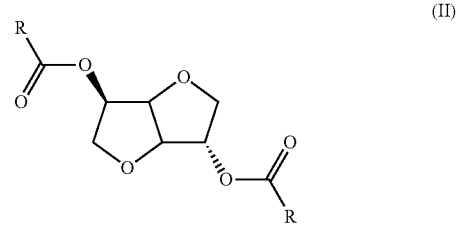

(II)

where R is a straight-chain or branched saturated alkyl group having 5 to 11 carbon atoms or a straight-chain or branched mono- or polyunsaturated alkenyl group having 5 to 11 carbon atoms.

5. The method of claim 4, wherein the thickening composition comprises at least one compound of the formula (I),
I) from 0.05 to 0.7 by weight of isosorbide and
II) from 0.1 to 1.0 by weight of the at least one isosorbide diester of the formula (II), in each case based on 1.0 part by weight of the at least one compound of the formula (I).

6. The method of claim 1, wherein the thickening composition comprises the at least one compound of the formula (I) in an amount of at least 30% by weight, in each case based on the total weight of the finished composition.

7. The method of claim 1, wherein the cosmetic, dermatological or pharmaceutical composition, the crop protection formulation, the washing or cleaning composition or the paint or coating comprises the at least one compound of the formula (I) in an amount of from 0.01 to 10.0% by weight, in each case based on the total weight of the finished cosmetic, dermatological or pharmaceutical composition, crop protection formulation, washing or cleaning composition or paint or coating.

8. The method of claim 1, wherein the cosmetic, dermatological or pharmaceutical composition, the crop protection formulation, the washing or cleaning composition or the paint or coating are formulated on an aqueous or aqueous-alcoholic basis or are present as emulsion or dispersion.

9. The method of claim 1, wherein the cosmetic, dermatological or pharmaceutical composition, the crop protection formulation, the washing or cleaning composition or the paint or coating have a pH of from 2 to 11.

* * * * *